United States Patent [19]

Kennis et al.

[11] Patent Number: 4,548,939

[45] Date of Patent: Oct. 22, 1985

[54] 1H-INDOL-3-YL CONTAINING 1,3-DIMETHYL-1H-PURINE-2,6-DIONES

[75] Inventors: Ludo E. J. Kennis, Turnhout; Jan Vandenberk, Beerse; Jozef M. Boey, Vosselaar, all of Belgium

[73] Assignee: Janssen Pharmaceutica N. V., Beerse, Belgium

[21] Appl. No.: 656,561

[22] Filed: Oct. 1, 1984

[51] Int. Cl.$^4$ ............... C07D 473/08; A61K 31/505
[52] U.S. Cl. ................................. 514/265; 544/268; 544/267; 544/265; 546/201; 514/323
[58] Field of Search ............. 544/268, 267, 265; 514/265

[56] References Cited

U.S. PATENT DOCUMENTS

| | | | |
|---|---|---|---|
| 3,980,658 | 9/1976 | Possanza et al. | 546/201 |
| 4,064,255 | 12/1977 | Champseix et al. | 546/201 |
| 4,196,209 | 4/1980 | Dumont et al. | 546/201 |
| 4,284,633 | 8/1981 | Friebe et al. | 514/265 |
| 4,299,832 | 11/1981 | Brown et al. | 544/267 |
| 4,342,870 | 8/1982 | Kennis et al. | 544/282 |
| 4,359,468 | 11/1982 | Freter et al. | 546/201 |
| 4,426,383 | 1/1984 | Sugimoto et al. | 544/267 |
| 4,443,451 | 4/1984 | Kennis et al. | 514/258 |

Primary Examiner—Donald G. Daus
Assistant Examiner—S. A. Gibson
Attorney, Agent, or Firm—Geoffrey G. Dellenbaugh

[57] ABSTRACT

1H-Indol-3-yl containing 1,3-dimethyl-1H-purine-2,6-diones having psychotropic activity.

6 Claims, No Drawings

1H-INDOL-3-YL CONTAINING 1,3-DIMETHYL-1H-PURINE-2,6-DIONES

BACKGROUND OF THE INVENTION

In European Pat. No. 71,738 there are described a number of piperidine and piperazine containing theophylline derivatives as compounds having various pharmacological activities. Further, a number of 4-[1H-indol-3-yl]piperidines are described in U.S. Pat. No. 3,980,658 and in U.S. Pat. No. 3,947,578 as compounds useful as tranquillizers respectively as neuroleptics, and in U.S. Pat. No. 4,359,468 and U.S. Pat. No. 4,342,870 as anti-allergics and hypotensives respectively as serotonin antagonists. The compounds of the present invention differ therefrom essentially by the fact that they invariably contain a 1,3-dimethyl-1H-purine-2,6-dione moiety connected to a 1H-indol-3-yl substituted piperidine or 3,6-dihydro-1(2H)-pyridine, and by their specific pharmacological properties.

DESCRIPTION OF THE PREFERRED EMBODIMENTS

This invention is concerned with novel 1H-indol-3-yl containing 1,3-dimethyl-1H-purine-2,6-diones which structurally may be represented by the formula

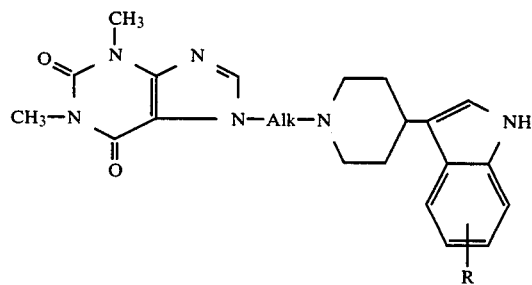

and the pharmaceutically acceptable acid addition salts thereof, wherein

Alk represents a bivalent lower alkyl radical;

R is hydrogen, lower alkyl, halo, lower alkyloxy, or hydroxy; the dotted line indicating that the double bond between the 3- and 4-carbon atoms of the piperidine nucleus is optional.

In the foregoing definitions the term "halo" is generic to fluoro, chloro, bromo and iodo; and "lower alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like.

The most preferred compounds are selected from the group consisting of 7-[2-[4-(1H-indol-3-yl)-1-piperidinyl]ethyl]-3,7-dihydro-1,3-dimethyl-1H-purine-2,6-dione and the pharmaceutically acceptable acid addition salts thereof.

The compounds of formula (I) can generally be prepared by reacting an intermediate of formula (II) with a piperidine of formula (III) following art-known alkylating procedures.

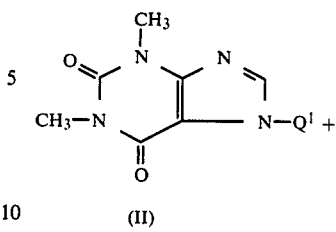

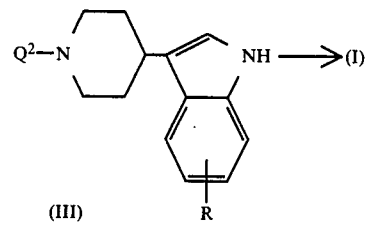

In (II) and (III), $Q^1$ and $Q^2$ are selected so that during the alkylation reaction the 1,3-dihydro-2,6-dioxo-1,2,3,6-tetrahydro-7H-purin-7-yl radical becomes connected via -Alk- to the substituted 1-piperidinyl or 3,6-dihydro-1(2H)-pyridinyl radical as defined in formula (I).

For example, the compounds of formula (I) can generally be prepared by N-alkylating an intermediate of formula (III) wherein $Q^2$ is hydrogen, said intermediate being represented by the formula (III-a) with a reagent of formula (II) wherein $Q^1$ represents -Alk-W, said reagent having the formula (II-a).

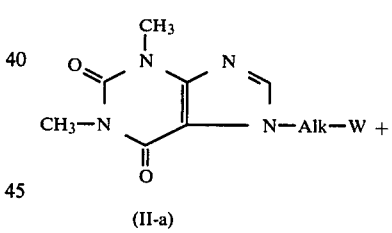

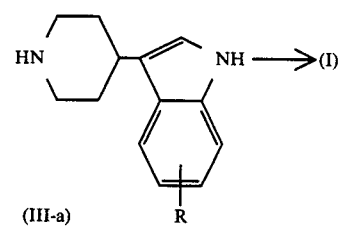

In (II-a) W represents an appropriate reactive leaving group such as, for example, halo, e.g., chloro, bromo or iodo, or a sulfonyloxy group, e.g. methylsulfonyloxy or 4-methylphenyl-sulfonyloxy.

Additionally, the compounds of formula (I) can also be prepared by N-alkylating an intermediate of formula (II) wherein $Q^1$ is hydrogen, said intermediate being represented by the formula (II-b) with an intermediate of formula (III) wherein $Q^2$ is -Alk -W, (III-b).

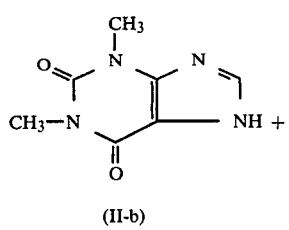

(II-b)

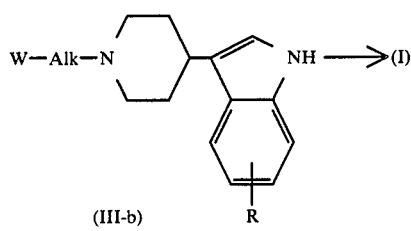

(III-b)

In (III-b) W has the previously defined meaning.

The alkylation reactions are conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; N,N-dimethylformamide (DMF); N,N-dimethylacetamide (DMA); nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of an iodide salt, preferably an alkali metal iodide, is appropriate. Somewhat elevated temperatures may enhance the rate of the reaction.

In all of the foregoing and in the following preparations, the reaction products may be isolated from the reaction mixture and, if necessary, further purified according to methodologies generally known in the art.

The compounds of formula (I) have basic properties and, consequently they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

The intermediates and starting materials in the foregoing preparations can be prepared following art-known procedures described in, for example, U.S. Pat. No. 4,064,255, No. 4,196,209 and in the references cited hereinabove in the "Background of the Invention" part.

The compounds of formula (I) and the pharmaceutically acceptable acid addition salts thereof are potent antagonists of a series of neurotransmittors and as a result they have useful pharmacological properties. For example, the compounds of formula (I) and their pharmaceutically acceptable acid addition salts possess apomorphine-, tryptamine- and norepinephrine antagonistic activity. Said activities are demonstrated in the following test procedures described hereafter and the experimental data therefrom are summarized in table 1.

The combined apomorphine (APO)-, tryptamine (TRY)- and norepinephrine (NOR) test in rats.

The experimental animals used in this test were adult male Wistar rats (weight 240±10 g). After an overnight fast, the animals were treated subcutaneously (1 ml/100 g) with an aqueous solution of the compound under investigation (time =zero) and put in isolated observation cages. Thirty minutes thereafter (time=30 minutes) 1.25 mg/kg of apomorphine hydrochloride (APO) was injected intravenously and the rats were observed over a 1 hour period for the presence or absence of the following apomorphine-induced phenomena: agitation and stereotypic chewing. At the end of this 1 hour period (time=90 minutes) the same animals were injected intravenously with 40 mg/kg of tryptamine (TRY) and the presence of the typical tryptamine-induced bilateral tonic seizures was noted. Two hours after pretreatment (time=120 minutes) finally, the same animals were challenged with 1.25 mg/kg intravenously of norephinephrine (NOR) and possible mortality was looked for up to 60 minutes later.

The table 1 gives the $ED_{50}$-values of a number of the compounds under consideration. As used herein, the $ED_{50}$-value represents the dose which protects 50% of the animals from apomorphine-, tryptamine- or norepinephrine-induced phenomena.

The compounds listed in table 1 are not given for the purpose of limiting the invention thereto but only to exemplify the useful pharmacological activities of all the compounds within the scope of formula (I).

TABLE 1

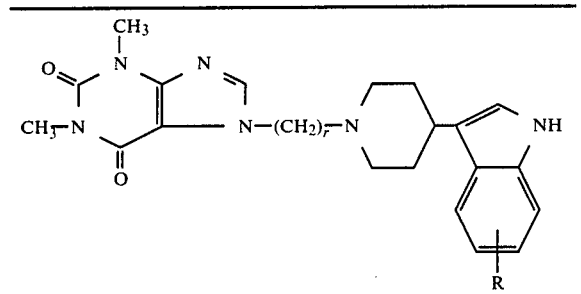

| Comp. No. | r | C=C | R | APO | TRY | NOR |
|---|---|---|---|---|---|---|
| 1 | 2 | C—C | H | 0.39 | 0.78 | 1.2 |
| 21 | 2 | C=C | H | — | 1.25 | 2.5 |
| 3 | 2 | C—C | 7-CH₃ | — | 5 | 1.25 |
| 5 | 2 | C—C | 5-F | 2.5 | 5 | 2.5 |
| 13* | 3 | C—C | H | — | 2.5 | 0.31 |
| 7 | 2 | C—C | 5-Cl | 1.25 | 1.25 | — |
| 17 | 3 | C=C | H | 5 | — | 1.25 |
| 18 | 4 | C=C | H | — | — | 0.10 |
| 10* | 3 | C—C | 7-CH₃ | — | — | 0.50 |
| 12 | 2 | C=C | 6-F | 1.25 | 0.63 | 1.25 |
| 14 | 3 | C—C | 6-F | 5 | 5 | 0.12 |
| 15** | 4 | C—C | H | — | — | 0.08 |
| 16 | 4 | C—C | 6-F | — | — | 0.04 |

*(E)-2-butenedioate (1:1)
**(E)-2-butenedioate (2:1)

Due to their pharmacological activities, the compounds of formula (I) and their pharmaceutically acceptable acid addition salts can be used in the treatment of warm-blooded animals suffering from psychotropic diseases. The subject compounds have also useful properties as sedating, anxiolytic, anti-aggressive and anti-stress agents and, consequently, they are useful to protect non-human warm-blooded animals, for example, in stress situations, e.g., during transport periods and the like situations. More particularly, the subject compounds are useful for manipulation, minor and major surgery, transport and grouping of cattle.

In view of the usefulness of the subject compounds in the treatment of psychotropic diseases and of their capability of effecting sedatic, anxiolytic, anti-agressive and anti-stress activities, the subject compounds may be formulated into various pharmaceutical forms for administration purposes.

To prepare the pharmaceutical compositions of this invention, an effective amount of the particular compound, in base or acid-addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

It is evident that the present invention provides a method of treating warm-blooded animals suffering from said psychotropic diseases or a method of treating warm-blooded animals by effecting sedatic, anxiolytic, anti-aggressive and anti-stress activities. Said method comprises the systemic administration of a psychotropically effective amount of a compound of formula (I) or a pharmaceutically acceptable acid addition salt thereof in admixture with a pharmaceutical carrier.

Suitable doses administered to subjects are varying from 0,001 mg/kg to 10 mg/kg body weight more preferably from 0.05 mg/kg to 0.5 mg/kg body weight.

The following examples are intended to illustrate and not to limit the scope of the present invention. Unless otherwise stated all parts therein are by weight.

EXAMPLES

EXAMPLE 1

A mixture of 5 parts of 7-(2-chloroethyl)-3,7-dihydro-1,3-dimethyl-1H-purine-2,6-dione, 4 parts of 3-(4-piperidinyl)-1H-indole, 8 parts of sodium carbonate, 1 part of potassium iodide and 120 parts of 4-methyl-2-pentanone was stirred and refluxed overnight. The reaction mixture was cooled, water was added and the layers were separated. The organic phase was dried, filtered and evaporated. The residue was purified by column-chromatography over silica gel using a mixture of trichloromethane and methanol (95:5 by volume) as eluent. The pure fractions were collected and the eluent was evaporated. The residue was crystallized from 4-methyl-2-pentanone, yielding 4 parts (50%) of 7-[2-[4-(1H-indol-3-yl)-1-piperidinyl]ethyl]-3,7-dihydro-1,3-dimethyl-1H-purine-2,6-dione; mp. 201.2° C. (compound 1).

EXAMPLE 2

A mixture of 3.65 parts of 7-(2-chloroethyl)-3,7-dihydro-1,3-dimethyl-1H-purine-2,6-dione, 3 parts of 3-(4-piperidinyl)-1H-indol-5-ol, 4.25 parts of sodium carbonate, 0.1 parts and potassium iodide and 200 parts of 4-methyl-2-pentanone was stirred and refluxed overnight. The whole was filtered while hot and the filtrate was evaporated. The residue was suspended in 45 parts of trichloromethane and 2.4 parts of methanol. The product was filtered off, washed with 16 parts of methanol and dried, yielding 2.5 parts (43%) of 3,7-dihydro-7-[2-[4-(5-hydroxy-1H-indol-3-yl)-1-piperidinyl]ethyl]-1,3-dimethyl-1H-purine-2,6-dione; mp. 232.5° C. (compound 2).

In a similar manner there were also prepared:
3,7-dihydro-1,3-dimethyl-7-[2-[4-(7-methyl-1H-indol-3-yl)-1-piperidinyl]ethyl]-1H-purine-2,6-dione; mp. 200.2° C. (compound 3);
7-[3-[4-(5-fluoro-1H-indol-3-yl)-1-piperidinyl]propyl]-3,7-dihydro-1,3-dimethyl)-1H-purine-2,6-dione (E)-2-butenedioate (1:1); mp. 232.3° C. (compound 4);
7-[2-[4-(5-fluoro-1H-indol-3-yl)-1-piperidinyl]ethyl]-3,7-dihydro-1,3-dimethyl-1H-purine-2,6-dione; mp. 168.4° C. (compound 5);
7-[3-[4-(5-chloro-1H-indol-3-yl)-1-piperidinyl]propyl]-3,7-dihydro-1,3-dimethyl-1H-purine-2,6-dione; mp. 105.8° C. (compound 6);
7-[2-[4-(5-chloro-1H-indol-3-yl)-1-piperidinyl]ethyl]-3,7-dihydro-1,3-dimethyl-1H-purine-2,6-dione; mp. 225.0° C. (compound 7);
3,7-dihydro-7-[2-[4-(5-methoxy-1H-indol-3-yl)-1-piperidinyl]ethyl]-1,3-dimethyl-1H-purine-2,6-dione; mp. 205.0° C. (compound 8);
3,7-dihydro-7-[3-[4-(5-methoxy-1H-indol-3-yl)-1-piperidinyl]propyl]-1,3-dimethyl-1H-purine-2,6-dione; mp. 104.4° C. (compound 9);

3,7-dihydro-1,3-dimethyl-7-[3-[4-(7-methyl-1H-indol-3-yl)-1-piperidinyl]-propyl]-1H-purine-2,6-dione (E)-2-butenedioate(1:1); mp. 228.1° C. (compound 10);

7-[2-[4-(5-bromo-1H-indol-3-yl)-3,6-dihydro-1(2H)-pyridinyl]ethyl]-3,7-dihydro-1,3-dimethyl-1H-purine-2,6-dione monohydrochloride; mp. 258.9° C. (compound 11); and 7-[2-[4-(6-fluoro-1H-indol-3-yl)-3,6-dihydro-1(2H)-pyridinyl]ethyl]-3,7-dihydro-1,3-dimethyl-1H-purine-2,6-dione; mp. 163.5° C. (compound 12).

EXAMPLE 3

A mixture of 4.5 parts of 7-(3-chloropropyl)-3,7-dihydro-1,3-dimethyl-1H-purine-2,6-dione monohydrochloride, 3 parts of 3-(4-piperidinyl)-1H-indol, 8 parts of sodium carbonate, 0.1 parts of sodium iodide and 240 parts of 4-methyl-2-pentanone was stirred and refluxed for 20 hours. The whole was filtered while hot and the filtrate was evaporated. The residue was purified by column chromatography over silica gel using a mixture of trichloromethane and methanol (92:8 by volume) as eluent. The pure fractions were collected and the eluent was evaporated. The residue was converted into the (E)-2-butenedioate salt in 2-propanol. The salt was filtered off and dried, yielding 3.9 parts (48%) of 3,7-dihydro-7-[3-[4-(1H-indol-3-yl)-1-piperidinyl]propyl]-1,3-dimethyl-1H-purine-2,6-dione (E)-2-butenedioate(1:1); mp. 222.7° C. (compound 13).

In a similar manner there were also prepared:

7-[3-[4-(6-fluoro-1H-indol-3-yl)-1-piperidinyl]propyl]-3,7-dihydro-1,3-dimethyl-1H-purine-2,6-dione; mp. 128.0° C. (compound 14);

3,7-dihydro-7-[4-[4-(1H-indol-3-yl)-1-piperidinyl]butyl]-1,3-dimethyl-1H-purine-2,6-dione (E)-2-butenedioate(2:1); mp. 227.7° C. (compound 15); and 7-[4-[4-(6-fluoro-1H-indol-3-yl)-1-piperidinyl]butyl]-3,7-dihydro-1,3-dimethyl-1H-purine-2,6-dione; mp. 151.8° C. (compound 16).

EXAMPLE 4

A mixture of 5 parts of 7-(3-chloropropyl)-3,7-dihydro-1,3-dimethyl-1H-purine-2,6-dione monohydrochloride, 4 parts of 3-(1,2,3,6-tetrahydro-4-pyridinyl)-1H-indole, 8 parts of sodium carbonate and 240 parts of 4-methyl-2-pentanone was stirred for 22 hours at reflux temperature. The whole was stirred till room temperature was reached. The product was filtered off and stirred in water. After filtration, the product was washed with water and stirred in water and an equivalent amount of acetic acid. The mixture was treated with ammonium hydroxide. The precipitated product was filtered off, washed with water and stirred in a mixture of acetonitrile and 2-propanol. The product was filtered off, washed with acetonitrile and dried, yielding 7 parts (98%) of 7-[3-[3,6-dihydro-4-(1H-indol-3-yl)-1(2H)-pyridinyl]propyl]-3,7-dihydro-1,3-dimethyl-1H-purine-2,6-dione; mp. 243.2° C. (compound 17).

In a similar manner there were also prepared: 7-[4-[3,6-dihydro-4-(1H-indol-3-yl)-1(2H)-pyridinyl]butyl]-3,7-dihydro-1,3-dimethyl-1H-purine-2,6-dione; mp. 198.3° C. (compound 18); and 7-[4-[4-(5-fluoro-1H-indol-3-yl)-1-piperidinyl]butyl]-3,7-dihydro-1,3-dimethyl-1H-purine-2,6-dione (E)-2-butenedioate(1:1); mp. 210.6° C. (compound 19).

EXAMPLE 5

A mixture of 6 parts of 7-(3-chloropropyl)-3,7-dihydro-3-dimethyl-1H-purine-2,6-dione monohydrochloride, 5 parts of 5-bromo-3-(1,2,3,6-tetrahydro-4-pyridinyl)-1H-indole monohydrate, 10 parts of sodium carbonate, 0.2 parts of sodium iodide and 135 parts of N,N-dimethylacetamide was stirred and heated overnight at 90° C. The reaction mixture was evaporated to dry. The residue was stirred in water. The product was extracted with trichloromethane. The extract was dried, filtered and evaporated. The residue was purified by column chromatography over silica gel using a mixture of trichloromethane and methanol (90:10 by volume) as eluent. The pure fractions were collected and the eluent was evaporated. The residue was crystallized from acetonitrile. The product was filtered off and dried, yielding 3.2 parts (36%) of 7-[3-[4-(5-bromo-1H-indol-3-yl)-3,6-dihydro-1(2H)-pyridinyl]propyl]-3,7-dihydro-1,3-dimethyl-1H-purine-2,6-dione; mp. 195.1° C. (compound 20).

EXAMPLE 6

A mixture of 3.8 parts of 7-(2-chloroethyl)-3,7-dihydro-1,3-dimethyl-1H-purine-2,6-dione, 3 parts of 3-(3,6-dihydro-1(2H)-pyridinyl)-1H-indole, 8 parts of sodium carbonate, 0.1 parts of potassium iodide and 270 parts of methylbenzene was stirred and refluxed for 20 hours. The reaction mixture was filtered while hot and the filtrate was evaporated. The residue was purified by column chromatography over silica gel using a mixture of trichloromethane and methanol (92:8 by volume) as eluent. The pure fractions were collected and the eluent was evaporated. The residue was crystallized from 2-propanone. The product was filtered off and dried in vacuo at 120° C., yielding 3.1 parts (51.6%) of 3,7-dihydro-7-[2-[3,6-dihydro-4-(1H-indol-3-yl)-1(2H)-pyridinyl]ethyl]-1,3-dimethyl-1H-purine-2,6-dione; mp. 196.5° C. (compound 21).

What is claimed is:

1. A chemical compound having the formula

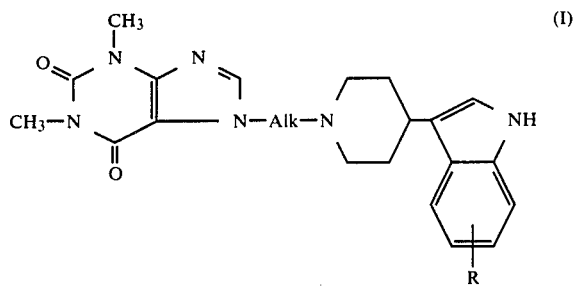

(I)

and a pharmaceutically acceptable acid addition salt thereof, wherein

Alk represents a bivalent lower alkyl radical;

R is hydrogen, lower alkyl, halo, lower alkyloxy or hydroxy; the dotted line indicating that the double bond between the 3- and 4-carbon atoms of the piperidine nucleus is optional.

2. A chemical compound selected from the group consisting of 7-[2-[4-(1H-indol-3-yl)-1-piperidinyl]ethyl]-3,7-dihydro-1,3-dimethyl-1H-purine-2,6-dione and the pharmaceutically acceptable acid addition salts thereof.

3. A psychotropically effective composition having sedating, anxiolytic, anti-aggressive and anti-stress properties useful in the treatment of non-human warm-blooded animals comprising a suitable pharmaceutical carrier and as active ingredient a sedating, anxiolytic, anti-aggressive and anti-stress effecting amount of a compound having the formula

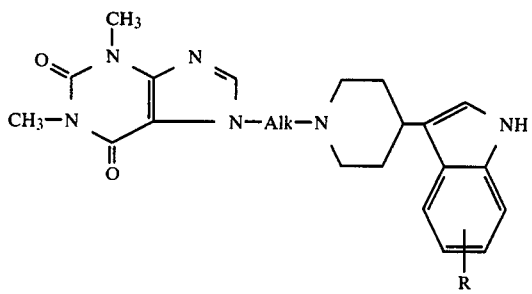

and a pharmaceutically acceptable acid addition salt thereof, wherein

Alk represents a bivalent lower alkyl radical;

R is hydrogen, lower alkyl, halo, lower alkyloxy or hydroxy; the dotted line indicating that the double bond between the 3- and 4-carbon atoms of the piperidine nucleus is optional.

4. A composition according to claim 3 wherein the compound is selected from the group consisting of 7-[2-[4-(1H-indol-3-yl-1-piperidinyl]ethyl]-3,7-dihydro-1,3-dimethyl-1H-purine-2,6-dione and the pharmaceutically acceptable acid addition salts thereof.

5. A method of treating non-human warm-blooded animals by effecting sedating, anxiolytic, anti-aggressive and anti-stress activities which method comprises the systemic administration to warm-blooded animals of a sedating, anxiolytic, anti-agressive and anti-stress effecting amount of a compound having the formula

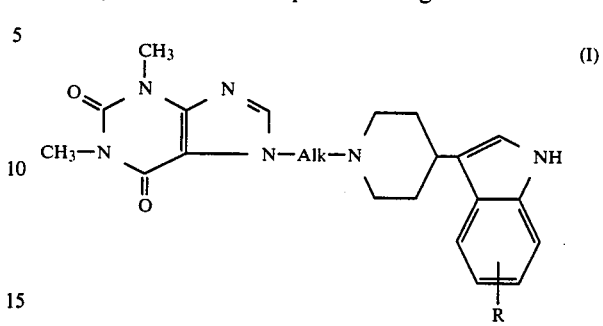

and a pharmaceutically acceptable acid addition salt thereof, wherein

Alk represents a bivalent lower alkyl radical;

R is hydrogen, lower alkyl, halo, lower alkyloxy or hydroxy; the dotted line indicating that the double bond between the 3- and 4-carbon atoms of the piperidine nucleus is optional.

6. A method according to claim 5, wherein the compound is selected from the group consisting of 7-[2-[4-(1H-indol-3-yl)-1-piperidinyl]ethyl]-3,7-dihydro-1,3-dimethyl-1H-purine-2,6-dione and the pharmaceutically acceptable acid addition salts thereof.

* * * * *

UNITED STATES PATENT AND TRADEMARK OFFICE
CERTIFICATE OF CORRECTION

PATENT NO. : 4,548,939

DATED : October 22, 1985

INVENTOR(S) : Kennis, et al.

It is certified that error appears in the above-identified patent and that said Letters Patent is hereby corrected as shown below:

Claims 1, 3, and 5 in the formula in each delete

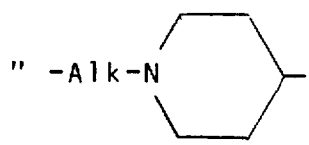 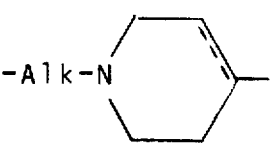

Signed and Sealed this

Twelfth Day of August 1986

[SEAL]

Attest:

DONALD J. QUIGG

Attesting Officer     Commissioner of Patents and Trademarks